United States Patent [19]
Cook et al.

[11] 4,415,658
[45] Nov. 15, 1983

[54] PROCESS FOR DECOMPOSING 2,4-DIHYDROXY-6-AMINO-S-TRIAZINE DERIVATIVES

[75] Inventors: Alasdair M. Cook, Wädenswil; Ralf Hütter, Gockhausen, both of Switzerland

[73] Assignee: Ciba-Geigy Corporation, Ardsley, N.Y.

[21] Appl. No.: 298,440

[22] Filed: Sep. 1, 1981

[30] Foreign Application Priority Data

Sep. 10, 1980 [CH] Switzerland ..................... 6796/80

[51] Int. Cl.$^3$ ..................... C12N 1/20; C12P 1/04; C12P 17/12; C12P 13/00; C12R 1/38
[52] U.S. Cl. ..................... 435/122; 435/128; 435/170; 435/253; 435/264; 435/874; 210/611; 210/909
[58] Field of Search ..................... 435/3, 253, 874, 122, 435/128, 262, 264, 170; 210/611, 909

[56] References Cited

U.S. PATENT DOCUMENTS 3,880,740  4/1975  Mimura et al. ..................... 435/262
4,247,645  1/1981  Meijer-Hoffman et al. ......... 435/262
4,274,955  6/1981  Zeyer et al. ......................... 435/122

OTHER PUBLICATIONS

Saldick, Applied Microbiology, 28, 1004–1008, (1974).
Plimmer et al., J. Agr. Food Chem., 19(3), 572–573, (1971).
Kearney et al., J. Agr. Food Chem., 13(4), 369–372, (1965).
Jensen et al., "Cyanuric Acid as Nitrogen Source for Micro-Organisms", Arch. Microbiol. 67, 1–5, (1969).
Laurence et al., "Analysis of Triazine Herbicides by Combined . . . ", J. Chromatog. 100, 175–179, (1974).

Primary Examiner—Esther M. Kepplinger
Attorney, Agent, or Firm—Frederick H. Rabin

[57] ABSTRACT

The invention relates to a process for decomposing 2,4-dihydroxy-6-amino-s-triazine derivatives in effluents. The essential feature of the process is that the effluent is brought into contact under aerobic conditions with either of the strains Pseudomonas sp. NRRL B-12228 or Pseudomonas sp. NRRL B-12229. It is likewise possible according to one variant of the process to convert 2-hydroxy-4,6-diamino-s-triazine derivatives present into 2,4-dihydroxy-6-amino-s-triazine derivatives by bringing the effluent into contact with Pseudomonas sp. NRRL B-12227.

23 Claims, No Drawings

PROCESS FOR DECOMPOSING 2,4-DIHYDROXY-6-AMINO-S-TRIAZINE DERIVATIVES

The present invention relates to a process for decomposing, in effluents, 2,4-dihydroxy-6-amino-s-triazine derivatives of the formula I

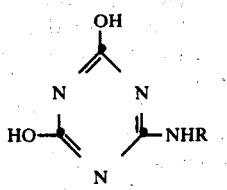

wherein R is an aliphatic or cycloaliphatic radical having 1 to 6 carbon atoms.

In the production of triazine herbicides, for example 2-ethylamino-4-isopropylamino-6-chloro-s-triazine (Atrazine), 2,4-bis-ethylamino-6-chloro-s-triazine (Simazine) or 2,4-bis-isopropylamino-6-chloro-s-triazine (Propazine), by reaction of cyanuric chloride with corresponding alkylamines, there occur effluents which contain, besides the desired herbicidal active substance, also various 6-hydroxy-alkylamino-s-triazines, such as 2-amino-4-ethylamino-6-hydroxy-s-triazine (N-ethylammeline), 2-amino-4-isopropylamino-6-hydroxy-s-triazine (N-isopropylammeline), 2,6-bis-hydroxy-4-ethylamino-s-triazine (N-ethylammelide) or 2,6-bis-hydroxy-4-isopropylamino-s-triazine (N-isopropylammelide). The decomposition of such compounds is desirable for ecological reasons.

It is known that alkylamino-s-triazines can be dealkylated by oxidation (J. Agr. Food Chem. 19 (3), 572–573, 1971). The amino-s-triazines formed in the process can be further converted by hydrolysis in an acid medium to cyanuric acid, which cannot be further decomposed hydrolytically.

Alkylamino-s-triazines of the aforementioned type can also be split directly, by energetic hydrolysis in an acid medium, into cyanuric acid and alkylamine (Journal of Chromatography 100, 175–179, 1974). There had also been an earlier report regarding the biological decomposition of 2,4-bis-alkylamino-6-chloro-s-triazines to give ammelide (J. Agr. Food Chem. 13, 369–372, 1965). The decomposition of impurities such as are present in the effluents from industrial plants producing triazine herbicides leads therefore, with application of the chemical methods known hitherto, merely to cyanuric acid. By use of the biological process mentioned above for the decomposition of 2,4-bis-alkylamino-6-chloro-s-triazines, the resulting end product of decomposition is on the other hand ammelide, which renders necessary a subsequent chemical hydrolysis to give cyanuric acid.

Cyanuric acid can be decomposed microbiologically (Arch. Microbiol. 67, 1–5, 1969; J. Environm. Qual. 4, 134–139, 1975; Appl. Microbiol. 28, 1004–1008, 1974; German Offenlegungsschriften Nos. 2,521,842 and 2,923,794); however, the processes are generally slow, or are limited to the decomposition of the cyanuric acid, without the strains effecting this being able also to attack amino-s-triazine derivatives which carry on the amino group an aliphatic or cycloaliphatic radical.

The processes mentioned in the foregoing for the microbial decomposition of the said amino-s-triazine derivatives are not applicable for practical purposes since the decomposition yields overall are too low. A further disadvantage is that in general there occurs no complete mineralisation of the compounds.

It is therefore the object of the present invention to provide a process for decomposing 2,4-dihydroxy-6-amino-s-triazine derivatives of the formula I, which process will have for practical purposes a sufficiently high decomposition yield.

It has now been found that strains of the bacterial genus Pseudomonas, namely Pseudomonas sp. NRRL B-12228 and Pseudomonas sp. NRRL B-12229, are able to utilise compounds of the formula I as the sole nitrogen source.

Suitable for the complete decomposition of compounds of the formula I into carbon dioxide and ammonia (in non-growing cultures) or into carbon dioxide and cellular substance (in growing cultures) is in particular the bacterial strain Pseudomonas sp. NRRL B-12228.

The process according to the invention for the decomposition of 2,4-dihydroxy-6-amino-s-triazine derivatives of the formula I which are contained in effluents comprises bringing the effluent, under aerobic conditions, into contact with either of the strains Pseudomonas sp. NRRL B-12228 or Pseudomonas sp. NRRL B-12229, in consequence of which the 2,4-dihydroxy-6-amino-s-triazine derivatives of the formula I which are contained in the effluent can be rapidly and completely decomposed.

The process according to the invention is suitable also for the complete decomposition of triazines in effluents which contain, in addition to 2,4-dihydroxy-6-amino-s-triazine derivatives of the formula I, also 2-hydroxy-4,6-diamino-s-triazine derivatives of the formula II

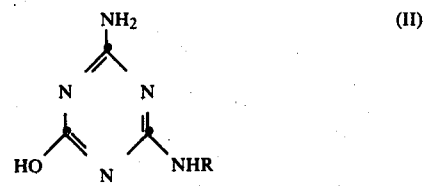

wherein R is an aliphatic or cycloaliphatic radical having 1 to 6 carbon atoms, in which process the effluent, before or during the decomposition of 2,4-dihydroxy-6-amino-s-triazine derivatives of the formula I, is brought into contact, for conversion of 2-hydroxy-4,6-diamino-s-triazine derivatives of the formula II present into 2,4-dihydroxy-6-amino-s-triazine derivatives of the formula I, under aerobic conditions with Pseudomonas sp. NRRL B-12227.

Particularly good results are obtained with the decomposition of 2,4-dihydroxy-6-alkylamino-s-triazine derivatives of the formula Ia

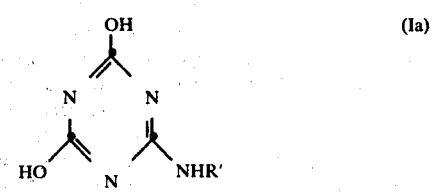

wherein R' is an alkyl group having 1 to 6 carbon atoms, as well as of 2-hydroxy-4-amino-6-alkylamino-s-triazine derivatives of the formula IIa

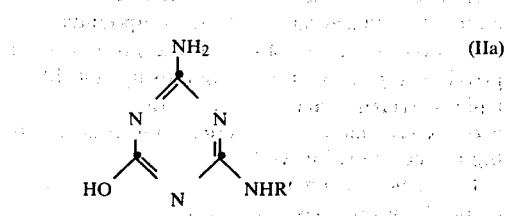

wherein R' is an alkyl group having 1 to 6 carbon atoms, especially however with the decomposition of compounds of the formula Ib

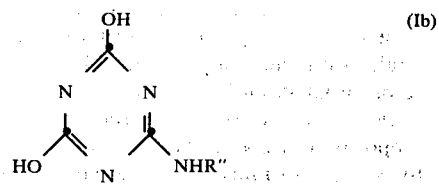

wherein R'' is an ethyl or isopropyl group, that is, of 2,4-dihydroxy-6-ethylamino-s-triazine (N-ethylammelide) and 2,4-dihydroxy-6-isopropylamino-s-triazine (N-isopropylammelide), as well as of compounds of the formula IIb

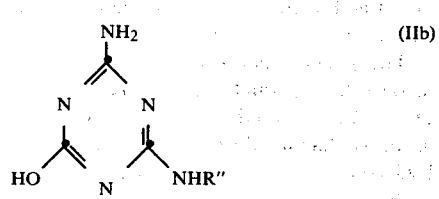

wherein R'' is an ethyl or isopropyl group, that is, of 2-hydroxy-4-amino-6-ethylamino-s-triazine (N-ethylammeline) and 2-hydroxy-4-amino-6-isopropylamino-s-triazine (N-isopropylammeline).

Three strains of Pseudomonas sp. to be used according to the invention were filed on the 18th July, 1980, at the Agricultural Research Culture Collection, Northern Regional Research Center (=NRRL), Peoria, Ill. 61604-US, and registered under the Serial Numbers B-12227, B-12228 and B-12229.

The strain Pseudomonas sp. NRRL B-12227 was isolated from the sewage sludge of the waste water purifying plant, Werdhölzli, Zürich (Switzerland).

The strains Pseudomonas sp. NRRL B-12228 and Pseudomonas sp. NRRL B-12229 were isolated from a mixture of soil samples which originated partly from the experimental fields of Ciba-Geigy AG in Bex and Vufflens (Switzerland), and partly from experimental fields of the Swiss Agricultural Research Station at Wädenswil (Switzerland), and which had received one to seven treatments with s-triazine herbicides.

The three strains Pseudomonas sp. NRRL B-12227, Pseudomonas sp. NRRL B-12228 and Pseudomonas sp. NRRL B-12229 have been identified as being Pseudomonas strains since they are strictly aerobic, oxidase-positive, mobile (rod-shaped) bacterial (approx. 0.5 to $1.5 \times 1$ to 3 μm), which grow without vitamins in the pH-range of 6 to 8, and can utilise both glucose and acetate as carbon source. Observations under the electron microscope moreover show a cell wall structure typical for gram-negative bacteria, and also a polar multitrichous arrangement of flagella. The organisms cannot be classified under any of the species described in Stanier et al. (Stanier, R. Y., N. J. Palleroni and M. Doudoroff; J. Gen. Microbiol. 43, 159–271, 1966). The strains Pseudomonas sp. NRRL B-12228 and Pseudomonas sp. NRRL B-12229 are very similar to one another, so that only the Pseudomonas sp. NRRL B-12228 strain is specified in the detailed description.

On nutrient agar plates, the strains grow at 30° C. within two days to 1 mm (Pseudomonas sp. NRRL B-12228) or 2 mm (Pseudomonas sp. NRRL B-12227) large, whitish-beige-coloured, dull (Pseudomonas sp. NRRL B-12227) or slimy-glossy (Pseudomonas sp. NRRL B-12228) colonies having discrete edges. The growth is good in the range of 24° to 37° C., whereas both strains grow only slowly below 20° C., and not at all from 41° C. upwards.

Further characteristics of the strains Pseudomonas sp. NRRL B-12227 and Pseudomonas sp. NRRL-12228 are listed below:

| Characteristic | Pseudomonas sp. NRRL B-12227 | Pseudomonas sp. NRRL B-12228 |
|---|---|---|
| number of flagella | >1 | >1 |
| fluorescent pigment | 0 | 0 |
| phenazine pigment | 0 | 0 |
| methionine requirement | 0 | 0 |
| dentrification | 0 | 0 |
| growth at 4° C. | 0 | 0 |
| growth at 41° C. | 0 | 0 |
| starch hydrolysis | + | + |
| oxidase reaction | + | + |
| arginine-dihydrolase reaction | 0 | 0 |
| utilisation of carbon sources: | | |
| D-glucose | + | + |
| trehalose | 0 | + |
| cellobiose | 0 | 0 |
| maltose | + | + |
| starch | + | + |
| inositol | 0 | 0 |
| 2-ketogluconate | 0 | + |
| maleate | 0 | + |
| glycolate | 0 | + |
| DL-lactate | + | + |
| adipate | + | + |
| testosterone | 0 | 0 |
| acetamide | 0 | 0 |
| D-tryptophane | + | + |
| p-hydroxybenzoate | + | + |
| glycerine | + | + |
| succinate | + | + |
| acetate | + | + |
| growth on McConkey agar | 0 | + |

The bacteria of the Pseudomonas genus to be used according to the invention are firstly grown on a suitable base medium, and subsequently added to aqueous solutions of the substrates to be decomposed; or they are grown directly on media which contain the substrates to be decomposed.

A suitable base medium is composed for example as follows:

| | |
|---|---|
| potassium phosphate buffer, pH 7.3 | 10 mM |
| magnesium sulfate heptahydrate | 0.25 mM |
| trace-element solution according to Pfennig and Lippert (Arch. Microbiol. 55, 245, 1966), supplemented with 100 mg per liter of calcium chloride dihydrate | 5 ml/liter |
| lactic acid | 10 mM |

| -continued | |
|---|---|
| nitrogen source | 2.5 mM of nitrogen. |

There can be used as nitrogen sources: ammonia, cyanuric acid, ammelide, ammeline or compounds of the formula I (for Pseudomonas sp. NRRL B-12228 and Pseudomonas sp. NRRL B-12229), or compounds of the formula II (for Pseudomonas sp. NRRL B-12227).

The process for decomposing compounds of the formula I can be carried out for example by inoculating an aqueous medium, in which are present the compounds in dissolved form together with suitable salts and a suitable carbon source, with cultures of the strain Pseudomonas sp. NRRL B-12228. Suitable salts are for example those given in the case of the base medium described in the foregoing; and suitable carbon sources are for example glucose, acetate or lactate. Carrying out the process with growing cells of Pseudomonas sp. NRRL B-12228 has proved particularly favourable.

The process can be performed in a corresponding manner by inoculating with Pseudomonas sp. NRRL B-12227 in order to convert compounds of the formula II into compounds of the formula I.

It is also possible to mix together separately pre-grown cultures of Pseudomonas sp. NRRL B-12228 and Pseudomonas sp. NRRL B-12227 in a ratio of 1:1 (cellular substance of Pseudomonas sp. NRRL B-12228: cellular substance of Pseudomonas sp. NRRL B-12227); to subsequently incubate the mixture in 10 mM of phosphate buffer, pH 7.3, and to then bring it into contact with the aqueous medium.

Pseudomonas sp. NRRL B-12229 can moreover be used in place of Pseudomonas sp. NRRL B-12228, but the Pseudomonas sp. NRRL B-12228 strain is clearly to be preferred.

The process according to the invention is further illustrated by the following Examples:

EXAMPLE 1

Decomposition of N-ethylammelide to carbon dioxide and cellular substance by growing cultures of Pseudomonas sp. NRRL B-12228

There is taken from a slant agar culture based on agar, which corresponds to the base medium given below, with the addition of 2% of agar (Difco Noble Agar), a specimen of the strain Pseudomonas sp. NRRL B-12228, and this is inoculated into a base medium of the following composition:

| potassium phosphate buffer, pH 7.3 | 10 mM |
|---|---|
| magnesium sulfate heptahydrate | 0.25 mM |
| trace-element solution according to Pfennig and Lippert (Arch. Microbiol. 55, 245, 1966), supplemented with 100 mg per liter of calcium chloride dihydrate | 5 ml/liter |
| lactic acid | 10 mM |
| N—ethylammelide | 0.6 mM |

The suspension is incubated on a rotary shaking machine (180 r.p.m.) at 30° C. Specimens are taken at intervals of about 1 hour, and these are used to trace the relative amount of bacterial by measurement of the optical density at 546 nm ($OD_{546}$), and the amount of N-ethylammelide remaining by high-pressure liquid chromatography (HPLC).

The test results are summarised in Table 1

TABLE 1

| Nitrogen source in medium (start of growing, 2.5 mM of N in each case) | (end of growing) | Growth yield (g of protein/mol of utilised N) | Rate of growth $\mu(h^{-1})$ | Spec. rate of decomposition (mkat/kg* of protein) |
|---|---|---|---|---|
| ammonia | no longer detectable | 43 | 0.29 | 1.9 |
| N—ethyl-ammelide | | 38 | — | — |

— = not determined
*kat = katal (= mol/sec)

It is clear from the data given above that the strain Pseudomonas sp. NRRL B-12228 is able to completely incorporate into its cellular substance the nitrogen present in the N-ethylammelide.

EXAMPLE 2

Decomposition of N-isopropylammelide to carbon dioxide and cellular substance by growing cultures of Pseudomonas sp. NRRL B-12228

The process with N-isopropylammelide as nitrogen source instead of N-ethylammelide is carried out using the experimental arrangement described in Example 1.

The test results are summarised in Table 2.

TABLE 2

| Nitrogen source in medium (start of growing, 2.5 mM of N in each case) | (end of growing) | Growth yield (g of protein/mol of utilised N) | Rate of growth $\mu(h^{-1})$ | Spec. rate of decomposition (mkat/kg of protein) |
|---|---|---|---|---|
| ammonia | no longer detectable | 43 | 0.29 | 1.9 |
| N—isopropyl-ammelide | | 44 | 0.28 | 0.44 |

It is clear from the given data that the strain Pseudomonas sp. NRRL B-12228 is able to completely incorporate into its cellular substance the nitrogen present in the N-isopropylammelide.

EXAMPLE 3

Deamination of N-ethylammeline to N-ethylammelide with Pseudomonas sp. NRRL B-12227

There is taken from a slant agar culture based on agar, which corresponds to the base medium given below, with the addition of 2% of agar (Difco Noble Agar), a specimen of the strain Pseudomonas sp. NRRL B-12227, and this is inoculated into a base medium of the following composition:

| potassium phosphate buffer, pH 7.3 | 10 mM |
|---|---|
| magnesium sulfate heptahydrate | 0.25 mM |
| trace-element solution according to Pfennig and Lippert (Arch. Microbiol. 55, 245, 1966), supplemented with 100 mg per liter of calcium chloride dihydrate | 5 ml/liter |
| lactic acid | 10 mM |
| N—ethylammeline | 0.5 mM |

The suspension is incubated on a rotating shaking machine (180 r.p.m.) at 30° C. Specimens are taken at intervals of about 1 hour, and in these specimens are traced the relative amount of bacteria by measurement of the optical density at 546 nm ($OD_{546}$), and the amount of N-ethylammeline remaining and also of the formed N-ethylammelide by high-pressure liquid chromatography (HPLC).

The test results are shown in Table 3.

TABLE 3

| Nitrogen source in medium | | Growth yield (g of protein/mol of utilised N) | Rate of growth $\mu(h^{-1})$ | Rate of conversion (mkat/kg of protein) |
|---|---|---|---|---|
| (start of growing) | (end of growing) | | | |
| N—ethyl-ammeline | N—ethyl-ammelide | 60 | 0.13 | 0.6 |

EXAMPLE 4

Deamination of N-isopropylammeline to N-isopropylammelide with Pseudomonas sp. NRRL B-12227

The process is carried out with N-isopropylammeline as nitrogen source instead of N-ethylammeline, the experimental arrangement used being as described in Example 3.

The test results are summarised in Table 4.

TABLE 4

| Nitrogen source in medium | | Growth yield (g of protein/mol of utilised N) | Rate of growth $\mu(h^{-1})$ | Rate of conversion (mkat/kg of protein) |
|---|---|---|---|---|
| (start of growing) | (end of growing) | | | |
| N—isopropyl-ammeline | N—isopropyl-ammelide | 60 | 0.12 | 0.5 |

EXAMPLE 5

Mineralisation of N-ethylammeline to carbon dioxide and ammonia by a mixture of dormant cells of Pseudomonas sp. NRRL B-12228 and Pseudomonas sp. NRRL B-12227

The strains Pseudomonas sp. NRRL B-12228 and Pseudomonas sp. NRRL B-12227 are grown under the conditions described in Examples 1 and 3. After the finish of growth of the individual strains, aliquot amounts of the two strains are mixed, and a suspension of 0.3 mg of protein/ml in 10 mM of potassium phosphate buffer, pH 7.3, is produced. To this buffer is added 0.5 mM of n-ethylammeline, and the formation of carbon dioxide and ammonia is traced and likewise the disappearance of the substrate.

The results are summarised in Table 5 (the duration of the test was 5 hours).

TABLE 5

| Organisms (stock mixture) | Amount of substrate | | Ammonia (formed up to end of test) | Carbon dioxide (formed up to end of test) |
|---|---|---|---|---|
| | (start of test) | (end of test) | | |
| A (0.15 mg of protein/ml and D (0.15 mg of protein/ml) | 0.5 mM of N—ethyl-ammeline | no longer detect-able | 2.3 mM | 83%[1] |

A: Pseudomonas sp. NRRL B-12227
D: Pseudomonas sp. NRRL B-12228

[1]Corresponds to percentage of the possible amount. Even with the use of bicarbonate, the carbon dioxide yield is merely 85%; thus, the yield given in the Table corresponds to practically 100%. The test is performed with $^{14}C$-labelled material (triazine ring-labelled).

The above data indicate clearly that the mixture of the strains Pseudomonas sp. NRRL B-12227 and Pseudomonas sp. NRRL B-12228 can efficiently decompose N-ethylammeline to carbon dioxide and ammonia.

EXAMPLE 6

Mineralisation of N-isopropylammeline to carbon dioxide and ammonia by a mixture of dormant cells of Pseudomonas sp. NRRL B-12228 and Pseudomonas sp. NRRL B-12227

The process with N-isopropylammeline as the nitrogen source in place of N-ethylammeline is carried out using the experimental arrangement described in Example 5.

The test results are summarised in Table 6 (the duration of the test was 5 hours).

TABLE 6

| Organisms (stock mixture) | Amount of substrate | | Ammonia (formed up to end of test) | Carbon dioxide (formed up to end of test)[1] |
|---|---|---|---|---|
| | (start of test) | (end of test) | | |
| A (0.15 mg of protein/ml and D (0.15 mg of protein/ml) | 0.5 mM of N—iso propyl-ammeline | no longer detect-able | 2.5 mM | 84% |

A: Pseudomonas sp. NRRL B-12227
D: Pseudomonas sp. NRRL B-12228

[1]Corresponds to percentage of the possible amount. Even with the use of bicarbonate, the carbon dioxide yield is merely 85%; the yield given in the Table thus corresponds to practically 100%. The test is carried out with $^{14}C$-labelled material (triazine ring-labelled).

The data given in the foregoing show clearly that the mixture of the strains Pseudomonas sp. NRRL B-12227 and Pseudomonas sp. NRRL B-12228 can efficiently decompose N-isopropylammeline to carbon dioxide and ammonia.

The present invention embraces, in addition to the aforementioned strains of Pseudomonas, also mutants thereof and other bacteria of the Pseudomonas genus usable for the purposes according to the invention, and likewise the use of these bacteria or mutants within the scope of the present invention.

What is claimed is:

1. A process for decomposing 2,4-dihydroxy-6-amino-s-triazine derivatives of the formula I

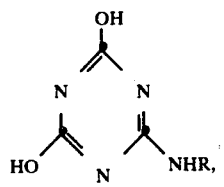

(I)

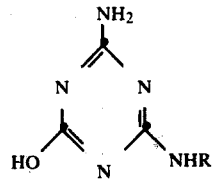

(II)

wherein R is an aliphatic or cycloaliphatic radical having 1 to 6 carbon atoms, in effluents containing said compounds, which process comprises bringing the effluents, under aerobic conditions, into contact with either of the strains Pseudomonas sp. NRRL B-12228 or Pseudomonas sp. NRRL B-12229 at temperatures of from 20° to 41° C.

2. A process according to claim 1, which is performed at temperatures of from 24° to 37° C.

3. A process according to claim 1, in which effluents which contain compounds of the formula Ia

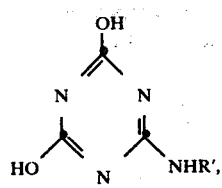

(Ia)

wherein R' is an alkyl group having 1 to 6 carbon atoms, are brought into contact with one of the Pseudomonas strains.

4. A process according to claim 2, in which effluents which contain compounds of the formula Ia

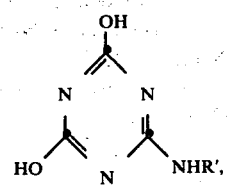

(Ia)

wherein R' is an alkyl group having 1 to 6 carbon atoms, are brought into contact with one of the Pseudomonas strains.

5. A process according to claim 1, which is performed with the strain Pseudomonas sp. NRRL B-12228.

6. A process according to claim 5, which is performed with growing cells of Pseudomonas sp NRRL B-12228.

7. A process according to claim 1, in which effluents which contain a compound of the formula Ib

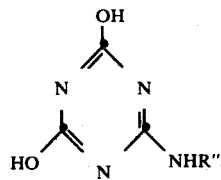

(Ib)

wherein R" is an ethyl or isopropyl group, is brought into contact with one of the Pseudomonas strains.

8. A process according to claim 2, in which effluents which contain a compound of the formula Ib wherein R" is an aethyl or isopropyl group, is brought into contact with one of the Pseudomonas strains.

9. A process for conversion of 2-hydroxy-4,6-diamino-s-triazine derivatives of formula II

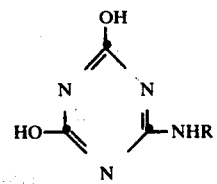

(Ib)

wherein R is an aliphatic or cycloaliphatic radical having 1 to 6 carbon atoms, contained in effluents, into a 2,4-dihydroxy-6-amino-2-triazine of the formula I,

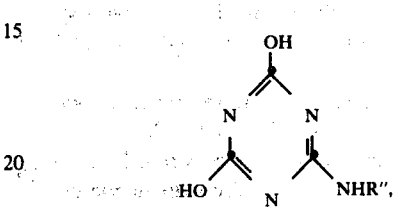

(I)

which process comprises bringing the effluents, under aerobic conditions, into contact with Pseudomonas ps. NRRL B-12227 at temperatures of from 20° to 41° C.

10. A process according to claim 9, in which process are converted 2-hydroxy-4,6-diamino-2-triazine derivatives of the formula IIa

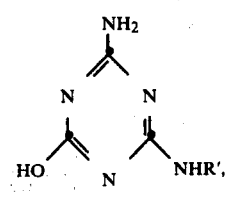

(IIa)

wherein R' is an alkyl group having 1 to 6 carbon atoms, into 2,4-dihydroxy-6-amino-s-triazine derivatives of the formula Ia

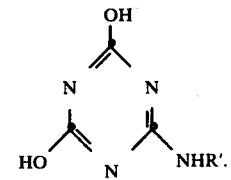

(Ia)

11. A process according to claim 9, which is performed at temperatures of from 24° to 37° C.

12. A process according to claim 10, which is performed at temperatures of from 24° to 37° C.

13. A process for purifying effluents containing ammeline derivatives of formula II

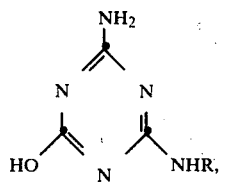

wherein R is an aliphatic or cycloaliphatic radical having 1 to 6 carbon atoms, by mineralization of said derivatives, in which process the effluents are brought into contact with a mixture of the strains Pseudomonas sp. NRRL B-12228 and Pseudomonas sp. NRRL B-12227 at temperatures of from 20° to 41° C.

14. A process according to claim 13, which is performed at temperatures of from 24° to 37° C.

15. An essentially pure culture of the strain Pseudomonas sp. NRRL B-12228, which effects the decomposition of 2,4-dihydroxy-6-amino-s-triazine derivatives of formula I

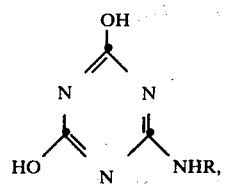

in which R is an aliphatic or cycloaliphatic radical having 1 to 6 carbon atoms.

16. An essentially pure culture of the strain Pseudomonas sp. NRRL B-12229, which effects the decomposition of 2,4-dihydroxy-6-amino-s-triazine derivatives of formula I

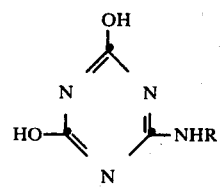

in which R is an aliphatic or cycloaliphatic radical having 1 to 6 carbon atoms.

17. An essentially pure culture of the strain Pseudomonas sp. NRRL B-12227, which effects the conversion of 2-hydroxy-4,6-diamino-s-triazine derivatives of formula II

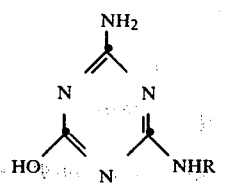

in which R is an aliphatic or cycloaliphatic radical having 1 to 6 carbon atoms.

18. A method of decomposing 2,4-dihydroxy-6-amino-s-triazine derivatives of the formula I

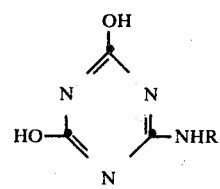

in which R is an aliphatic or cycloaliphatic radical having 1 to 6 carbon atoms, in effluents, which method comprises treating the effluents with an essentially pure culture of the strains Pseudomonas sp. NRRL B-12228 or Pseudomonas sp. NRRL B-12229 or of a mutant of these strains.

19. A method according to claim 18 using the strain Pseudomonas sp. NRRL B-12228.

20. A method according to claim 18 using the strain Pseudomonas sp. NRRL B-12229.

21. A method of decomposing 2,4-dihydroxy-6-amino-s-triazine derivaties of the formula I,

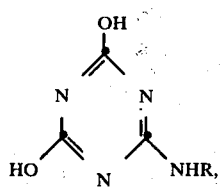

in which R is an aliphatic or cycloaliphatic radical having 1 to 6 carbon atoms, in effluents, which method comprises treating the effluents with an essentially pure culture of the strains Pseudomonas sp. NRRL B-12228 or Pseudomonas sp. NRRL B-12229.

22. A method of converting 2-hydroxy-4,6-diamino-s-triazine derivatives of formula II

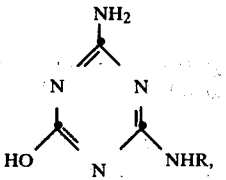

in which R is an aliphatic or cycloaliphatic radical having 1 to 6 carbon atoms, in effluents into 2,4-dihydroxy-6-amino-s-triazine of the formula I

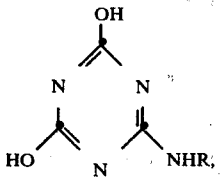

in which R is an aliphatic or cycloaliphatic radical having 1 to 6 carbon atoms, which method comprises treating the effluents with an essentially pure culture of the strain Pseudomonas sp. NRRL B-12227.

23. A method of purifying effluents containing ammeline derivatives of formula II

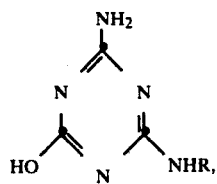

(II)

in which R is an aliphatic or cycloaliphatic radical having 1 to 6 carbon atoms, by mineralization of said derivatives, which method comprises treating the effluents with a mixture of essentially pure cultures of the strains Pseudomonas sp. NRRL B-12228 and Pseudomonas sp. NRRL B-12227.

* * * * *

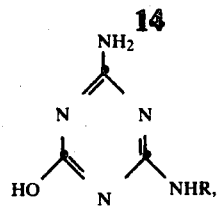

(II)

in which R is an aliphatic or cycloaliphatic radical having 1 to 6 carbon atoms, by mineralization of said derivatives, which method comprises treating the effluents with a mixture of essentially pure cultures of the strains Pseudomonas sp. NRRL B-12228 and Pseudomonas sp. NRRL B-12227.

* * * * *